(12) United States Patent
Shibata et al.

(10) Patent No.: US 11,659,854 B2
(45) Date of Patent: *May 30, 2023

(54) METHOD FOR IMPARTING BODY TASTE TO FOOD

(71) Applicant: FUJI OIL HOLDINGS INC., Osaka (JP)

(72) Inventors: Munehisa Shibata, Izumisano (JP); Takayasu Motoyama, Sakai (JP); Ryota Inoue, Sakai (JP)

(73) Assignee: FUJI OIL HOLDINGS INC., Osaka (JP)

(*) Notice: Subject to any disclaimer, the term of this patent is extended or adjusted under 35 U.S.C. 154(b) by 526 days.

This patent is subject to a terminal disclaimer.

(21) Appl. No.: 16/628,307

(22) PCT Filed: Jul. 6, 2018

(86) PCT No.: PCT/JP2018/025677
§ 371 (c)(1),
(2) Date: Jan. 3, 2020

(87) PCT Pub. No.: WO2019/013122
PCT Pub. Date: Jan. 17, 2019

(65) Prior Publication Data
US 2020/0178586 A1      Jun. 11, 2020

(30) Foreign Application Priority Data

Jul. 13, 2017 (JP) .............. JP2017-137172

(51) Int. Cl.
| | | |
|---|---|---|
| *A61K 38/08* | (2019.01) | |
| *C07K 7/06* | (2006.01) | |
| *A23L 27/21* | (2016.01) | |
| *C07K 5/093* | (2006.01) | |
| *C07K 5/113* | (2006.01) | |
| *A23L 11/65* | (2021.01) | |
| *A23L 11/50* | (2021.01) | |
| *A23L 11/45* | (2021.01) | |
| *A23L 2/38* | (2021.01) | |

(52) U.S. Cl.
CPC .............. *A23L 27/21* (2016.08); *A23L 2/38* (2013.01); *A23L 11/45* (2021.01); *A23L 11/50* (2021.01); *A23L 11/65* (2021.01); *C07K 5/0819* (2013.01); *C07K 5/1021* (2013.01); *C07K 7/06* (2013.01); *A23V 2002/00* (2013.01)

(58) Field of Classification Search
CPC .................. A61K 38/08; C07K 7/06
See application file for complete search history.

(56) References Cited

U.S. PATENT DOCUMENTS

| | | | |
|---|---|---|---|
| 5,780,090 | A | 7/1998 | Frerot et al. |
| 8,173,605 | B2 | 5/2012 | Ohsu et al. |
| 8,399,417 | B2 | 3/2013 | Nagasaki et al. |
| 8,420,144 | B2 | 4/2013 | Eto et al. |
| 8,541,368 | B2 | 9/2013 | Lau et al. |
| 8,541,379 | B2 | 9/2013 | Miyaki et al. |
| 9,395,376 | B2 | 7/2016 | Ohsu et al. |
| 9,420,813 | B2 | 8/2016 | Nagasaki et al. |
| 9,446,141 | B2 | 9/2016 | Lynch et al. |
| 9,486,505 | B2 | 11/2016 | Lau et al. |
| 9,486,506 | B2 | 11/2016 | Lau et al. |
| 9,822,064 | B2 | 11/2017 | Lynch et al. |
| 9,844,226 | B2 | 12/2017 | Futaki et al. |
| 9,845,283 | B2 | 12/2017 | Lynch et al. |
| 9,988,430 | B2 | 6/2018 | Reedtz-Runge et al. |
| 10,834,946 | B2 | 11/2020 | Didzbalis et al. |
| 10,856,562 | B2 | 12/2020 | Didzbalis et al. |
| 2009/0239310 | A1 | 9/2009 | Ohsu et al. |
| 2010/0120698 | A1 | 5/2010 | Nagasaki et al. |
| 2010/0136197 | A1 | 6/2010 | Eto et al. |
| 2010/0183792 | A1 | 7/2010 | Nagasaki et al. |
| 2011/0097805 | A1 | 4/2011 | Ohsu et al. |
| 2012/0034364 | A1 | 2/2012 | Futaki et al. |
| 2012/0277168 | A1 | 11/2012 | Miyaki et al. |
| 2013/0079278 | A1 | 3/2013 | Lau et al. |
| 2013/0288958 | A1 | 10/2013 | Lau et al. |
| 2014/0205729 | A1 | 7/2014 | Didzbalis et al. |
| 2015/0182594 | A1 | 7/2015 | Lau et al. |
| 2015/0342231 | A1 | 12/2015 | Didzbalis et al. |
| 2016/0030589 | A1 | 2/2016 | Lynch et al. |
| 2016/0102129 | A1 | 4/2016 | Reedtz-Runge et al. |
| 2016/0347706 | A1 | 12/2016 | Lynch et al. |
| 2016/0347730 | A1 | 12/2016 | Lynch et al. |
| 2016/0347812 | A1 | 12/2016 | Lau et al. |
| 2019/0254318 | A1 | 8/2019 | Didzbalis et al. |
| 2019/0274334 | A1 | 9/2019 | McGrane et al. |
| 2021/0076715 | A1 | 3/2021 | Didzbalis et al. |

FOREIGN PATENT DOCUMENTS

| | | |
|---|---|---|
| BR | 9606540 | 6/1998 |
| CN | 106544381 | 3/2017 |

(Continued)

OTHER PUBLICATIONS

Extended European Search Report dated Feb. 22, 2021 in corresponding European Patent Application No. 18832487.5.

(Continued)

*Primary Examiner* — Julie Ha

(74) *Attorney, Agent, or Firm* — Wenderoth, Lind & Ponack, L.L.P.

(57) ABSTRACT

A substance which adds body to a food product, and a body-adding agent for food products that uses the substance are provided. More specifically, the body adding agent for food products is characterized by having as an active component a peptide, or a salt thereof, that is characterized in that the γ-glutamyl bond number is 2-4 and the peptide chain length is the γ-glutamyl bond number +1 to +2, a food product manufacturing method that uses the peptide, and a method for adding body to a food product, characterized by adding the peptide are provided.

12 Claims, 3 Drawing Sheets

(56) References Cited

FOREIGN PATENT DOCUMENTS

| | | |
|---|---|---|
| CN | 106977583 | 7/2017 |
| CN | 107090013 | 8/2017 |
| CN | 107114752 | 9/2017 |
| CN | 107118258 | 9/2017 |
| CN | 107226835 | 10/2017 |
| CN | 107226837 | 10/2017 |
| CN | 107226838 | 10/2017 |
| CN | 107312067 | 11/2017 |
| CN | 107365356 | 11/2017 |
| CN | 107411023 | 12/2017 |
| CN | 107459555 | 12/2017 |
| JP | 60-9465 | 1/1985 |
| JP | 10-507086 | 7/1998 |
| JP | 2001-211880 | 8/2001 |
| JP | 2009-514791 | 4/2009 |
| JP | 2014-527975 | 10/2014 |
| JP | 2015-097474 | 5/2015 |
| JP | 2016-504051 | 2/2016 |
| JP | 2016-518339 | 6/2016 |
| WO | 2008/139945 | 11/2008 |
| WO | 2008/139946 | 11/2008 |
| WO | 2010/114022 | 10/2010 |
| WO | 2011/081185 | 7/2011 |
| WO | 2011/081186 | 7/2011 |
| WO | 2013/133404 | 9/2013 |
| WO | 2017/181062 | 10/2017 |
| WO | 2018/079848 | 5/2018 |

OTHER PUBLICATIONS

Burkhardt et al., "γ-Peptides of Glutamic Acid and Some of Their Properties", Archives of Biochemisuy and Biophysics, Academic Press, 1961, vol. 94, No. 11, pp. 32-34.
Szewczuk et al., "Specificity of γ-Glutamyl Cyclotransferase", Canadian Journal of Biochemistry, 1975, vol. 53, No. 6, pp. 706-712.
Search Report and Wiitten Opinion dated Jul. 30, 2021 in corresponding Singapore Application No. 11202000135P, 12 pages.
Office Action dated Nov. 11, 2021 in corresponding Korean Patent Application No. 10-2020-7001977, with English Machine Translation, 17 pages.
Nishimura et al., "Science of 'Koku' of food, Its current situation and prospects", Chemistry and Biology, 2016, vol. 54, No. 2, pp. 102-108, with English Translation.
International Search Report dated Oct. 9, 2018 in International (PCT) Patent Application No. PCT/JP2018/025677, with English Translation.
International Preliminary Report on Patentability dated Jan. 14, 2020 in International (PCT) Patent Application No. PCT/JP2018/025677.
Notice of Reasons for Refusal dated Jan. 21, 2020 in corresponding Japanese Patent Application No. 2019-184501, with English Translation.
Office Action dated Aug. 24, 2021 in corresponding Brazilian Application No. BR112020000373-5, with English Summary, 7 pages.
Official Notice dated Sep. 22, 2022, in corresponding Vietnamese Patent Application No. 1-2020-00743, with English translation, 6 pages.

Fig. 2

Umami (Initial to Middle)

|  | Panelist 1 | Panelist 2 | Panelist 3 | Panelist 4 | Panelist 5 | Panelist 6 | Panelist 7 | Avg. | SD |
|---|---|---|---|---|---|---|---|---|---|
| Control | 3 | 3 | 3 | 3 | 3 | 3 | 3 | 3.0 |  |
| γ-Glu-Tyr | 4 | 3 | 4 | 4 | 3 | 3 | 3.5 | 3.5 | 0.5 |
| γ-Glu-γ-Glu-Tyr | 4 | 4 | 3 | 4 | 4 | 4 | 5 | 4.0 | 0.6 |
| γ-Glu-γ-Glu-γ-Glu-Tyr | 4 | 5 | 3 | 4 | 5 | 4 | 4 | 4.1 | 0.7 |
| γ-Glu-γ-Glu-γ-Glu-γ-Glu-Tyr | 4 | 4 | 4 | 3 | 4 | 4 | 4 | 3.9 | 0.4 |
| γ-Glu-Val-Gly | 3 | 4 | 3 | 3 | 4 | 5 | 3 | 3.6 | 0.8 |

Umami (Middle to After)

|  | Panelist 1 | Panelist 2 | Panelist 3 | Panelist 4 | Panelist 5 | Panelist 6 | Panelist 7 | Avg. | SD |
|---|---|---|---|---|---|---|---|---|---|
| Control | 3 | 3 | 3 | 3 | 3 | 3 | 3 | 3.0 |  |
| γ-Glu-Tyr | 4 | 4 | 4 | 4 | 4 | 3 | 4 | 3.9 | 0.4 |
| γ-Glu-γ-Glu-Tyr | 5 | 4 | 4 | 3 | 4 | 4 | 3 | 3.9 | 0.7 |
| γ-Glu-γ-Glu-γ-Glu-Tyr | 5 | 5 | 3 | 3 | 4 | 4 | 4 | 4.0 | 0.8 |
| γ-Glu-γ-Glu-γ-Glu-γ-Glu-Tyr | 4 | 4 | 2 | 3 | 4 | 5 | 4 | 3.7 | 1.0 |
| γ-Glu-Val-Gly | 4 | 5 | 5 | 5 | 5 | 5 | 4.5 | 4.8 | 0.4 |

Sweet taste (Initial to Middle)

|  | Panelist 1 | Panelist 2 | Panelist 3 | Panelist 4 | Panelist 5 | Panelist 6 | Panelist 7 | Avg. | SD |
|---|---|---|---|---|---|---|---|---|---|
| Control | 3 | 3 | 3 | 3 | 3 | 3 | 3 | 3.0 |  |
| γ-Glu-Tyr | 4 | 4 | 3 | 3 | 3 | 4 | 3.5 | 3.5 | 0.5 |
| γ-Glu-γ-Glu-Tyr | 3 | 4 | 5 | 4 | 4 | 4 | 4 | 4.0 | 0.6 |
| γ-Glu-γ-Glu-γ-Glu-Tyr | 4 | 4 | 4 | 4 | 5 | 4 | 5 | 4.3 | 0.5 |
| γ-Glu-γ-Glu-γ-Glu-γ-Glu-Tyr | 4 | 4 | 4 | 3 | 4 | 4 | 4 | 3.9 | 0.4 |
| γ-Glu-Val-Gly | 4 | 4 | 3 | 3 | 3 | 4 | 4 | 3.6 | 0.5 |

Sweet taste (Middle to After)

|  | Panelist 1 | Panelist 2 | Panelist 3 | Panelist 4 | Panelist 5 | Panelist 6 | Panelist 7 | Avg. | SD |
|---|---|---|---|---|---|---|---|---|---|
| Control | 3 | 3 | 3 | 3 | 3 | 3 | 3 | 3.0 |  |
| γ-Glu-Tyr | 4 | 4 | 4 | 3 | 4 | 4 | 4 | 3.9 | 0.4 |
| γ-Glu-γ-Glu-Tyr | 3 | 4 | 4 | 3 | 4 | 4 | 4 | 3.7 | 0.5 |
| γ-Glu-γ-Glu-γ-Glu-Tyr | 4 | 5 | 4 | 4 | 5 | 4 | 4 | 4.3 | 0.5 |
| γ-Glu-γ-Glu-γ-Glu-γ-Glu-Tyr | 4 | 4 | 3 | 3 | 4 | 3 | 4 | 3.6 | 0.5 |
| γ-Glu-Val-Gly | 3 | 5 | 4 | 4 | 5 | 5 | 4 | 4.3 | 0.8 |

|  | Panelist 1 | Panelist 2 | Panelist 3 | Panelist 4 | Panelist 5 | Panelist 6 | Panelist 7 | Panelist 8 | Avg. | SD |
|---|---|---|---|---|---|---|---|---|---|---|
| (γ-Glu)3Tyr | 4 | 5 | 4 | 4 | 5 | 4 | 4 | 4 | 4.3 | 0.5 |
| (γ-Glu)3Ala | 4 | 4 | 3 | 3 | 3 | 3 | 4 | 3 | 3.4 | 0.5 |
| (γ-Glu)3Gly | 3 | 3 | 3 | 3 | 4 | 3 | 3 | 3 | 3.1 | 0.4 |
| (γ-Glu)3Glu | 3 | 4 | 4 | 3 | 4 | 4 | 3 | 3 | 3.5 | 0.5 |
| (γ-Glu)3Gln | 3 | 3 | 3 | 3 | 3 | 4 | 3 | 4 | 3.3 | 0.5 |
| (γ-Glu)3Cys | 3 | 3 | 3 | 3 | 4 | 2 | 3 | 3 | 3.0 | 0.5 |
| (γ-Glu)3Asp | 3 | 3 | 3 | 4 | 4 | 4 | 3 | 3 | 3.4 | 0.5 |
| (γ-Glu)3Asn | 3 | 3 | 2 | 3 | 3 | 4 | 4 | 4 | 3.3 | 0.7 |
| (γ-Glu)3Arg | 4 | 5 | 4 | 3 | 5 | 4 | 4 | 4 | 4.1 | 0.6 |
| (γ-Glu)3His | 3 | 3 | 3 | 3 | 4 | 4 | 4 | 4 | 3.5 | 0.5 |
| (γ-Glu)3Ile | 3 | 3 | 3 | 3 | 4 | 3 | 4 | 4 | 3.4 | 0.5 |
| (γ-Glu)3Leu | 3 | 2 | 3 | 3 | 4 | 4 | 3 | 4 | 3.3 | 0.7 |
| (γ-Glu)3Lys | 3 | 3 | 2 | 3 | 3 | 4 | 4 | 3 | 3.1 | 0.6 |
| (γ-Glu)3Met | 3 | 3 | 2 | 3 | 3 | 3 | 4 | 3 | 3.0 | 0.5 |
| (γ-Glu)3Phe | 3 | 4 | 3 | 3 | 4 | 3 | 4 | 3 | 3.4 | 0.5 |
| (γ-Glu)3Pro | 3 | 3 | 3 | 3 | 4 | 3 | 3 | 3 | 3.1 | 0.4 |
| (γ-Glu)3Trp | 3 | 3 | 2 | 3 | 4 | 3 | 3 | 4 | 3.1 | 0.6 |
| (γ-Glu)3Ser | 3 | 3 | 3 | 3 | 4 | 3 | 4 | 4 | 3.4 | 0.5 |
| (γ-Glu)3Thr | 3 | 3 | 2 | 3 | 3 | 3 | 3 | 3 | 2.9 | 0.4 |
| (γ-Glu)3Val | 3 | 4 | 3 | 3 | 3 | 4 | 3 | 4 | 3.4 | 0.5 |
| (γ-Glu)2Val | 3 | 2 | 3 | 3 | 3 | 3 | 4 | 4 | 3.1 | 0.6 |
| (γ-Glu)2GluTyr | 3 | 3 | 3 | 3 | 4 | 3 | 4 | 4.5 | 3.4 | 0.6 |

METHOD FOR IMPARTING BODY TASTE TO FOOD

TECHNICAL FIELD

Related Application

The present application claims the benefit of priority of application No. 2017-137172 filed to the Japan Patent Office on Jul. 13, 2017, said application is incorporated herein by reference in its entirety.

The present invention relates to a peptide. More specifically, the present invention relates to a peptide which may impart a body taste to a food.

Background Art

In general, deliciousness of food is said to be based on a balance of various factors such as taste, flavor, and texture. Among them, "taste" is one of the most important factors that determine the quality of food. And, it is widely recognized that the "taste" of food includes all kind of tastes including the five basic tastes expressed by sweetness, saltiness, acidity, bitterness, and umami.

Meanwhile, the use frequency of "koku" of foods that cannot be expressed only by the above five basic tastes has increased in recent years. "Koku" is defined as "taste which is generated from a lot of stimuli related to taste, flavor, and texture (richness, complexity, thickness), and it is felt when these stimuli are well-balanced, filled and maintained in the mouth" (Non-Patent Document 1). "Taste" which fulfils this definition is called as "kokumi" and "Kokumi means a taste that cannot be expressed with the five basic tastes, and means a taste that enhances not only the basic tastes but also marginal tastes of the basic tastes, such as thickness, growth (mouthfulness), persistence and harmony" (Patent Document 1).

The "kokumi" influences the deliciousness of the food. Deliciousness is added to a food by giving "kokumi" having a suitable strength for each food. Therefore, imparting/enhancing "kokumi" becomes one of the important points in making foods.

Glutathione (γ-Glu-Cys-Gly) has long been known as a substance that can impart "kokumi" to a food (Patent Document 2). In recent years, various γ-glutamyl peptides (Patent Document 1), γ-glutamyl-2-aminobutyric acid (γ-Glu-Abu) (Patent Document 3), γ-Glutamylnorvaline (γ-Glu-Nva) (patent document 4), and γ-glutamylnorvalylglycine (γ-Glu-Nva-Gly) (patent document 5) have been found by screening with using calcium receptor stimulating activity as an index.

Here, the taste changes with the lapse of time after eating, and is referred to as "initial taste", "middle taste", and "aftertaste" in order from immediately after eating. Among the above-mentioned various peptides, it is disclosed that γ-Glu-Abu and γ-Glu-Nva impart kokumi of the first taste, and γ-Glu-Nva-Gly imparts kokumi of the middle-after taste (Patent Documents 4 and 5).

Meanwhile, various γ-glutamyl peptides disclosed in Patent Document 1 having calcium receptor stimulating activity are said to improve the "body taste" of sweeteners by mixing with sweet substances (Patent Document 6). According to Patent Document 6, the "body taste" means that "the sweet substance has harmony and richness mainly in initial taste and middle taste when eating the sweet substance".

The above references and references listed herein are incorporated herein by reference.

PRIOR ART DOCUMENTS

Patent Documents

Patent Document 1: JP 2009-514791 A
Patent Document 2: JP S60-9465 A
Patent Document 3: WO 2010/114022 A
Patent Document 4: WO 2011/081185 A
Patent Document 5: WO 2011/081186 A
Patent Document 6: WO 2008/139946 A
Patent Document 7: JP 2001-211880 A

Non-Patent Documents

Non-Patent Document 1: Toshihide Nishimura et. al., Chemistry and Biology, Vol. 54, No. 2, p 102-108 (2016)

SUMMARY OF INVENTION

Problems to be Solved by Invention

In a design of food taste, an addition of a so-called body taste, mainly from the initial taste to the middle taste, is an important issue, as well as an addition of thickness and persistence of from the middle taste to the aftertaste. There is a demand for the development of a substance which may impart or enhance the so-called body taste, mainly from the initial taste to the middle taste.

As described above, various peptides which enhance kokumi have been found using calcium receptor activity as an index, but many of these impart a thickness and persistence of from the middle taste to aftertaste. In addition substances which enhance initial taste are excellent in the rise of the initial taste, but do not give a sufficient body taste for general taste. In this way, there are still few substances that can sufficiently give a body taste to a food.

An object of the present invention is to provide a new substance capable of imparting a body taste to a food, and to provide a body taste-imparting agent for food using said substance.

Means for Solving Problems

As a result of intensive study in order to solve the above problems with other approaches than the screening method using the calcium receptor activity as an index, the inventors have found that, among various peptides, certain peptides having a plurality of γ-glutamyl bindings may surprisingly impart a strong body taste mainly from the initial taste to middle taste to a food. The present invention has been completed by the findings.

That is, the present invention relates to:
(1) A body taste-imparting agent for a food, including a peptide having a γ-glutamyl bond number of 2 to 4 and a peptide chain length of γ-glutamyl bond number +1 to +2, or a salt thereof, as an active ingredient;
(2) The body taste-imparting agent of (1), where all γ-glutamyl bonds are continuous from N-terminus of the peptide;
(3) The body taste-imparting agent of (2), where C-terminus of the peptide is an amino acid or amino acid derivative which binds to glutamic acid with γ-glutamyl bond;
(4) A body taste-imparting agent for a food, including one or two or more peptides selected from the group consisting of a peptide consisting of γ-Glu-γ-Glu-X (X is an amino acid or amino acid derivative, the same shall apply hereinafter), a peptide consisting of γ-Glu-γ-Glu-γ-Glu-X, and a peptide consisting of γ-Glu-γ-Glu-γ-Glu-γ-Glu-X, or a salt thereof, as an active ingredient;

(5) The body taste-imparting agent of (4), where X is selected from the group consisting of Tyr, Ala, Glu, Gln, Asp, Asn, Arg, His, Ile, Leu, Phe, Ser, and Val;

(6) A method for producing a food, including adding a peptide having a γ-glutamyl bond number of 2 to 4 and a peptide chain length of γ-glutamyl bond number +1 to +2, or a salt thereof, to a food or a raw material of the food, where a body taste is imparted to the food;

(7) A method for imparting a body taste to a food, including adding a peptide having a γ-glutamyl bond number of 2 to 4 and a peptide chain length of γ-glutamyl bond number +1 to +2, or a salt thereof, to a food or a raw material of the food.

Effect of Invention

The present invention enables to impart a body taste to a food. In addition, the present invention enables to provide a substance which may impart a body taste to a food.

BRIEF DESCRIPTION OF DRAWINGS

FIG. 2 It is a figure showing detailed data of the sensory evaluation of Example 2.

MODE FOR CARRYING OUT INVENTION

As used herein, "food" refers to all kinds of food including beverage. In other words, the term "food" includes a beverage unless specifically specified as "except beverage". In one embodiment of the present invention, the food may be "food including beverage", "food excluding beverage", or "beverage".

As used herein, the quantity ratio (concentration, etc.) is a ratio based on weight unless otherwise specified. That is, for example, "%" means "% by weight (w/w)" unless otherwise specified, and "ppm" means "ppm (w/w)" unless otherwise specified. In the present invention, the "concentration at the time of eating" of a certain component means the concentration of the component in the food when the food containing the component is eaten.

As used herein, when a base, an amino acid, or the like is represented by an abbreviation, it is basically based on an abbreviation standardized by IUPAC or a common abbreviation in the field. Typical examples are shown below:
Gly: Glycine
Ala: Alanine
Val: Valine
Leu: Leucine
Ile: Isoleucine
Ser: Serine
Thr: Threonine
Cys: Cysteine
Met: Methionine
Glu: Glutamic acid
Asp: Aspartic acid
Lys: Lysine
Arg: Arginine
His: Histidine
Phe: Phenylalanine
Tyr: Tyrosine
Trp: Tryptophan
Pro: Proline
Asn: Asparagine
Gln: Glutamine
Orn: Ornithine
Sar: Sarcosine
Cit: Citrulline
Nva: Norvaline
Nle: Norleucine
Abu: α-Aminobutyric acid
Hyp: Hydroxyproline
Hse: Homoserine As used herein, for example, "γ-Glu-X" means that Glu and X are bonded via a carboxyl group at the γ-position of glutamic acid. As used herein, "X" means any amino acid or amino acid derivative unless otherwise specified.

Figure 1:
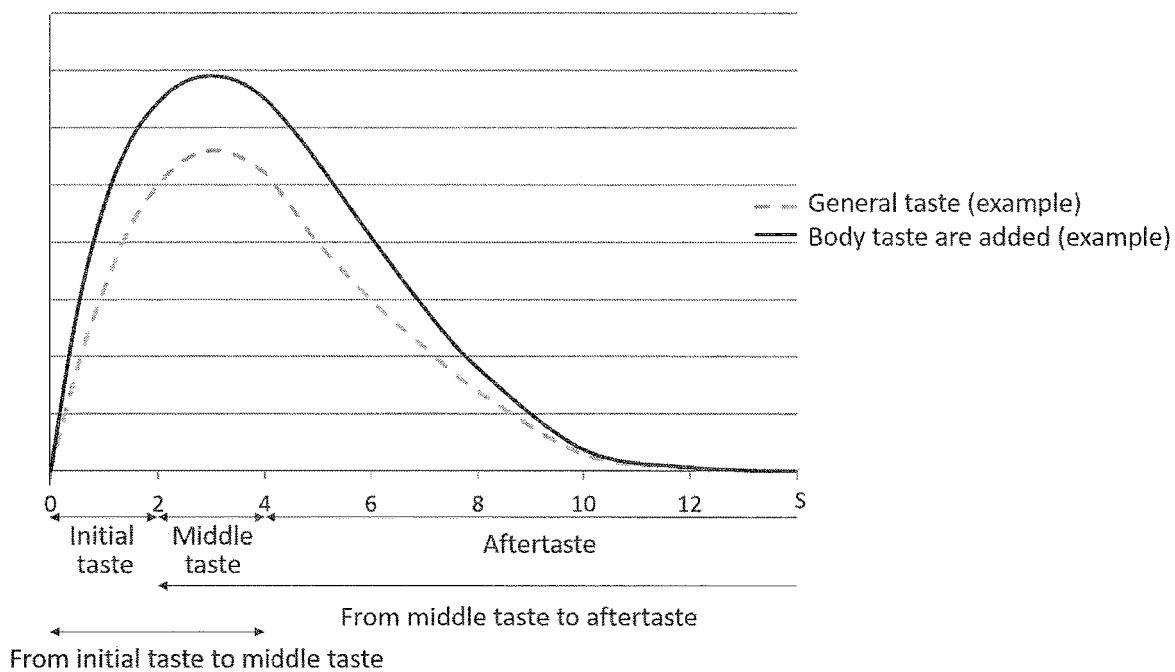
FIG. 1 It is a figure which represents a typical example of imparting a body taste to a food.

A "body taste" used herein means that taste having a harmony and richness mainly from the initial taste to middle taste when eating. The "body taste" in Patent Document 6 relates to sweetness, but in the present invention, it is not limited to sweetness, and refers to a harmony and richness of general taste. More specifically, imparting "body taste" means that the initial taste and middle taste are mainly enhanced and a rich feeling is imparted to around a portion where a strong taste is felt in general taste. In addition, it is more preferable that the initial taste is mainly enhanced and the middle taste and the aftertaste are also enhanced. Further, persistence of the aftertaste may or may not be enhanced, but preferably the persistence of aftertaste is not enhanced. A typical example of giving a body taste is as shown in FIG. 1, but is not limited thereto.

(Body Taste-Imparting Agent for Food)

In one embodiment, the present invention provides a body taste-imparting agent for a food, including a peptide having a γ-glutamyl bond number of 2 to 4 and a peptide chain length of γ-glutamyl bond number +1 to +2 (hereinafter referred to as γ-glutamyl peptide of this embodiment), or a salt thereof.

The γ-glutamyl peptide of this embodiment is typically a peptide represented by:

$$Z\text{-}(\gamma\text{-Glu})_n\text{-}Y\text{-}(\gamma\text{-Glu})_m\text{-}X\text{—}W \quad (1).$$

Here, X represents any amino acid or amino acid derivative. And, W, Y, and Z are each independently absent or represent any amino acid or amino acid derivative. The total number of W, X, Y, and Z (o) is 1 or 2. And, n and m are each independently an integer of 1 to 3, and n+m represents the number of γ-glutamyl bonds and is 2 to 4. And, n+m+o represents the peptide chain length, and is n+m+1 or n+m+2.

In one embodiment, all γ-glutamyl bonds in the γ-glutamyl peptide of this embodiment are continuous. More specifically, the γ-glutamyl peptide of this embodiment is a peptide represented by:

$$Z\text{-}(\gamma\text{-Glu})_n\text{-}X\text{—}Y \quad (2)$$

Here, X represents any amino acid or amino acid derivative. And, Y and Z are each independently absent or represent any amino acid or amino acid derivative. The total number of X, Y and Z (p) is 1 or 2. And, n is an integer of 2 to 4 and represents the number of γ-glutamyl bonds. And, n+p indicates the peptide chain length and is n+1 or n+2.

In another embodiment, all γ-glutamyl bonds are continuous from the N-terminal in the γ-glutamyl peptide of the present invention. More specifically, the peptide is a peptide represented by:

$$(\gamma\text{-Glu})_n\text{-X—Y} \quad (3)$$

Here, X represents any amino acid or amino acid derivative. And, Y is absent or represents any amino acid or amino acid derivative. And, n is an integer of 2 to 4 and represents the number of γ-glutamyl bonds. The peptide chain length is n+1 or n+2.

In yet another embodiment, the C-terminus of the peptide is an amino acid or amino acid derivative which binds to glutamine acid with γ-glutamyl bond in the γ-glutamyl peptide of this embodiment. Specifically, W in the embodiment of the chemical formula (1), Y in the embodiment of the chemical formula (2), or Y in the embodiment of the chemical formula (3) is absent, and a peptide represented by:

$$Z\text{-}(\gamma\text{-Glu})_n\text{-Y-}(\gamma\text{-Glu})_m\text{-X} \quad (4)$$

$$Z\text{-}(\gamma\text{-Glu})_n\text{-X} \quad (5)$$

$$(\gamma\text{-Glu})_n\text{-X} \quad (6),$$

and preferably, is an embodiment of chemical formula (6) above.

More specific examples of the γ-glutamyl peptide of the chemical formula (6) of this aspect include γ-Glu-γ-Glu-X, γ-Glu-γ-Glu-γ-Glu-X, or γ-Glu-γ-Glu-γ-Glu-γ-Glu-X, and more preferred examples include γ-Glu-γ-Glu-γ-Glu-X. In addition, these γ-glutamyl peptides may be used alone or in combination of two or more as active ingredients.

The amino acid or amino acid derivative represented by W, X, Y, and Z is not particularly limited, and includes any amino acid or amino acid derivative that may be used in a food. The amino acid and amino acid derivative may be any of D-form, L-form, and mixtures thereof, but is usually L-form. Specific examples of the amino acid include neutral amino acid such as Gly, Ala, Val, Leu, Ile, Ser, Thr, Cys, Met, Asn, Gln and Pro; acidic amino acid such as Asp and Glu; basic amino acid such as Lys, Arg and His; aromatic amino acids such as Phe, Tyr and Trp; Orn, Sar, Cit, Nva, Nle, Abu, Hyp, Hse and tert-Leu. In a certain embodiment, X is selected from the group consisting of Val, Leu, Ile, Ser, Thr, Cys, Met, Asp, Lys, Arg, His, Phe, Tyr, Trp, Pro, Asn, Orn, Cit, Nva, Nle, Abu, Hyp and Hse. In still another embodiment, X is selected from the group consists of Ile, Ser, Thr, Cys, Met, Asp, Lys, Arg, His, Trp, Pro, Asn, Orn, Cit, Nva, Nle, Abu, Hyp and Hse. Specific examples of the amino acid derivative include N-γ-nitroarginine, S-allylcysteine, S-methylcysteine, taurine, cycloleucine, 2-methylalanine and penicillamine. Examples of preferred amino acid include Tyr, Ala, Gly, Glu, Gln, Asp, Asn, Arg, His, Ile, Leu, Lys, Phe, Pro, Trp, Ser or Val, more preferably, Tyr, Ala, Glu, Gln, Asp, Asn, Arg, His, Ile, Leu, Phe, Ser or Val, still more preferably, Tyr, Ala, Glu, Asp, Arg, His, Ile, Phe, Ser or Val, further more preferably, Tyr, Glu, Arg or His, still further more preferably, Tyr or Arg. An example of one preferred amino acid is Tyr.

Examples included in the chemical formula (6) include (γ-Glu)$_{2\text{-}4}$-Tyr (embodiment example 6).

Examples included in the chemical formula (5) include the compound of Embodiment 6 and other examples include Gly-(γ-Glu)$_{2\text{-}4}$-Tyr (embodiment example 5).

Examples included in the above chemical formula (4) include the compound of embodiment example 5, and other examples include γ-Glu-Gly-(γ-Glu)$_{1\text{-}3}$-Tyr, (γ-Glu)$_2$-Gly-(γ-Glu)$_{1\text{-}2}$-Tyr, (γ-Glu)$_3$-Gly-γ-Glu-Tyr (embodiment example 4).

In addition, Example included in the chemical formula (3) include the compound of Embodiment Example 6, and other examples include (γ-Glu)$_{2\text{-}4}$-Gly-Tyr (Embodiment Example 3).

Examples included in the chemical formula (2) include the compounds of Embodiments 3 and 5 (Embodiment 2).

Examples included in the chemical formula (1) include the compounds of Embodiments 2 and 4 (Embodiment Example 1).

In the compounds exemplified above, Gly or Tyr exemplified as amino acid may be easily substituted with any other amino acid or amino acid derivative.

A method for obtaining and producing the γ-glutamyl peptide of this embodiment or a salt thereof is not particularly limited, and a commercially available product may be used as long as it is commercially available. Alternatively, it may be produced by a method of chemical synthesis or a method using an enzymatic reaction.

Examples of the method of chemical synthesis of the γ-glutamyl peptide of this embodiment include a solid phase method using a peptide synthesizer, or a liquid phase method. Examples of the method of producing the γ-glutamyl peptide of this embodiment using an enzymatic reaction include a method using γ-glutamyl transpeptidase described in Patent Document 7. A commercially available enzyme having γ-glutamyl transpeptidase activity may also be used. In addition, as a kind of enzymatic reaction, it may be produced by culturing a microorganism capable of producing the component and recovering the desired component from the culture solution or cell. As a more specific example of the enzymatic reaction, the γ-glutamyl peptide of this embodiment may be obtained by reacting glutamine and a desired amino acid with γ-glutamyltranspeptidase.

The obtained peptide may be used as it is, or may be purified by a known method such as ion exchange chromatography, reverse phase high performance liquid chromatography and affinity chromatography. For example, a purified product having a peptide purity of 50% or more, 70% or more, 90% or more, or 95% or more may be used.

The γ-glutamyl peptide of this embodiment may be used in a free form or a salt form. The salt of the γ-glutamyl peptide of this embodiment may be any food-acceptable salt. For example, for acidic group such as carboxyl group, ammonium salt, salt with alkali metal such as sodium and potassium, salt with divalent metal such as magnesium and calcium, aluminum salt, zinc salt, salt with organic amine such as triethylamine, ethanolamines, morpholine, pyrrolidine, piperidine, piperazine and dicyclohexylamine, and salt with basic amino acid such as arginine and lysine. For basic group in the presence of basic group, salt with inorganic acid such as hydrochloric acid, sulfuric acid, phosphoric acid, nitric acid and hydrobromic acid, salt with organic carboxylic acid such as acetic acid, citric acid, benzoic acid, maleic acid, fumaric acid, tartaric acid, succinic acid, tannic acid, butyric acid, hybenzic acid, pamoic acid, enanthic acid, decanoic acid, teocric acid, salicylic acid, lactic acid, oxalic acid, mandelic acid and malic acid, and salt with organic sulfonic acid such as methanesulfonic acid, benzenesulfonic acid and p-toluenesulfonic acid.

The body taste-imparting agent for a food of this embodiment contains one or two or more γ-glutamyl peptides of this embodiment or a salt thereof as an active ingredient. The body taste-imparting agent for a food of this embodiment may be consisting of the γ-glutamyl peptide of the present embodiment or a salt thereof, a crude product, or a purified product thereof. Moreover, the body taste-imparting agent for a food of this embodiment may contain other food ingredients in addition to the above active ingredient, as long as the body taste-imparting to a food is not prevented. Examples of such food ingredient include seasoning such as vinegar, miso, soy sauce and amino acid, acidulant, sweetener, bitter, spice, preservative, colorant, flavor, salt, sugar, fat, antioxidant, vitamin, stabilizer and thickener.

A form of the body taste-imparting agent for a food of this embodiment is not particularly limited, and may be various forms depending on the application. For example, it may be liquid, syrup, paste, cube, granule or powder.

A content and content ratio of each component in the body taste-imparting agent for a food of this embodiment are not particularly limited as long as the body taste-imparting effect is obtained, and may be adjusted according to various conditions, such as the type of each component, the eating concentration, and the used amount of the body taste-imparting agent of this embodiment.

A content of the γ-glutamyl peptide of the present embodiment in the body taste-imparting agent for a food of the present embodiment is not particularly limited. And, for example, the lower limit may be 1 ppm (0.0001%) or more, 10 ppm (0.001%) or more, 100 ppm (0.01%) or more, 1000 ppm (0.1%) or more, 1% or more, 10% or more, or 20% or more, and the upper limit may be 100% or less, 99.9% or less, 50% or less, 10% or less, or 1% or less. Examples of preferable content of the γ-glutamyl peptide include 10 to 100%, 15 to 100%, 20 to 100%, 30 to 100%, 40 to 100%, 50 to 100%, 60 to 100%, 70 to 100%, 80 to 100%, 85 to 100%, 90 to 100%, 95 to 100%, 75 to 99%, 75 to 95%, 80 to 99%, 80 to 95%. When the component forms a salt, the content of the γ-glutamyl peptide is calculated by converting the mass of the salt into the mass of an equimolar free form.

When the body taste-imparting agent of this embodiment is added to a food, the amount added is not particularly limited as long as the body taste-imparting effect is obtained. It may be adjusted as appropriate according to various conditions such as content of each component in the body taste-imparting agent for a food of this embodiment and a form of intake of the food composition. For example, the body taste-imparting agent for a food of this embodiment may be added in an amount of 0.1 ppm to 5000 ppm (0.5%) as a conversion value to the amount of γ-glutamyl peptide to the food or raw material thereof. Examples of preferred addition amount include, for example, 0.5 to 5000 ppm, 1 to 5000 ppm, 10 to 5000 ppm, 100 to 5000 ppm, 250 to 5000 ppm, 1000 to 5000 ppm, 0.1 to 3000 ppm, 0.5 to 3000 ppm, 1 to 3000 ppm, 10 to 3000 ppm, 100 to 3000 ppm, 250 to 3000 ppm, 1000 to 3000 ppm, 0.1 to 1000 ppm, 0.5 to 1000 ppm, 1 to 1000 ppm, 10 to 1000 ppm, 100 to 1000 ppm, 250 to 1000 ppm, 0.1 to 500 ppm, 0.5 to 500 ppm, 1 to 500 ppm, 10 to 500 ppm and 100 to 500 ppm.

A food to which the body taste-imparting agent for a food of this embodiment is added is not particularly limited, and various foods and compositions that can be eaten and consumed are widely included. The food may be a natural product or a processed food that is not a natural product. Preferably, the food is a non-natural product. Examples of the food include beverage such as soft drink, fruit juice, milk beverage, soy milk beverage, tea beverage, alcoholic beverage and soup; processed food such as ham, sausage and hamburger; fish processed food such as kamaboko (boiled fish paste) and chikuwa (a tube-shaped fish paste cake); soy protein product such as granular soy protein and powdered soy protein; processed soy protein product such as gan-modoki (deep-fried bean curd containing bits of various kinds of vegetables), tofu, atsuage (deep-fried tofu), tofu hamburger; fat such as edible fat, margarine, shortening and emulsified fat; dairy product such as butter, fermented milk, milk powder, cream and cheese; confectionery or confectionery material such as chocolate, candy, gum, gummi, snack, cookie, whipped cream, custard cream, flour paste, cake, pudding, jelly, bun, dumpling; seasoning such as sauce, mayonnaise, ketchup, soy sauce and ponzu sauce; bread, and noodle. The body taste-imparting agent of this embodiment may be used for foods with various flavors such as Japanese-style food, Western-style food, Chinese-style food, Asian-style food and ethnic food. More preferred flavors include Japanese-style food, Western-style food and Chinese-style food. Specific examples of preferred food include seasoning such as miso, soy sauce, noodle soup and sesame sauce; various soup such as vegetable soup, seafood soup, ramen soup, chicken soup, tom yam kung and curry soup; various sauce such as cheese sauce, white sauce, demiglace sauce, meat sauce and oyster sauce; egg product such as mayonnaise; dairy product such as dairy product, fermented dairy product and sour milk beverage; coffee beverage; confectionery such as chocolate and cream; soybean product such as soy food, soy milk and soy protein product. Specific examples of more preferred food product include miso, vegetable soup such as tomato and corn, seafood soup such as clam chowder, cheese sauce, white sauce, demiglace sauce, meat sauce, egg product, sesame sauce, dairy product, fermented milk Product, sour milk beverage, coffee beverage, chocolate, cream, soybean food, soymilk and soy protein product.

(Novel γ-glutamyl peptide)

In another aspect, the present invention also provides a novel γ-glutamyl peptide. More specifically, this aspect provides γ-glutamyl tripeptide, γ-glutamyl tetrapeptide or γ-glutamyl pentapeptide. As a more specific example, the novel γ-glutamyl tripeptide is represented by γ-Glu-γ-Glu-X (where X represents any amino acid or amino acid derivative), the novel γ-glutamyl tetrapeptide is represented by γ-Glu-γ-Glu-γ-Glu-X (where X represents any amino acid or amino acid derivative), a novel γ-glutamylpentapeptide is represented by γ-Glu-γ-Glu-γ-Glu-γ-Glu-X (where X represents any amino acid or amino acid derivative). Any amino acid or amino acid derivative represented by X is not particularly limited, and includes any amino acid or amino acid derivative that may be used in a food. The amino acid and amino acid derivative may take any of D-form, L-form, and mixtures thereof, but is usually L-form. Specific examples of amino acid include neutral amino acid such as Gly, Ala, Val, Leu, Ile, Ser, Thr, Cys, Met, Asn, Gln, Pro, acidic amino acid such as Asp and Glu, basic amino acid such as Lys, Arg and His, aromatic amino acid such as Phe, Tyr and Trp, Orn, Sar, Cit, Nva, Nle, Abu, Hyp, Hse and tert-Leu. Specific examples of the amino acid derivative include N-γ-nitroarginine, S-allylcysteine, S-methylcysteine, taurine, cycloleucine, 2-methylalanine and penicillamine. In a certain embodiment, X is selected from the group consisting of Tyr, Ala, Gly, Glu, Gln, Asp, Asn, Arg, His, Ile, Leu, Lys, Phe, Pro, Trp, Ser, Val, Orn, Cit, Nva, Nle, Abu, Hyp and Hse. In another embodiment, X is selected from the group consisting of Tyr, Ala, Glu, Gln, Asp, Asn, Arg, His, Ile, Leu, Phe, Ser, Val, Orn, Cit, Nva, Nle, Abu, Hyp and Hse. In still another embodiment, X is selected from the group consisting of Tyr, Ala, Glu, Asp, Arg, His, Ile, Phe, Ser, or Val, Orn, Cit, Nva, Nle, Abu, Hyp, and Hse. Examples of further preferred amino acid include Tyr, Ala, Glu, Asp, Arg, His, Ile, Phe, Ser, or Val, more preferably Tyr, Glu, Arg, or His, and even more preferably Tyr or Arg. An example of one preferred amino acid is Tyr.

Examples of the method of chemical synthesis of the novel γ-glutamyl peptide of this embodiment include a solid phase method using a peptide synthesizer, or a liquid phase method. Examples of the method of producing the novel γ-glutamyl peptide of this embodiment using an enzymatic reaction include a method using γ-glutamyl transpeptidase described in Patent Document 7. A commercially available enzyme having γ-glutamyl transpeptidase activity may also be used. In addition, as a kind of enzymatic reaction, it may be produced by culturing a microorganism capable of producing the component and recovering the desired component from the culture solution or cell. As a more specific example of the enzymatic reaction, the novel γ-glutamyl peptide of this embodiment may be obtained by reacting glutamine and a desired amino acid with γ-glutamyltranspeptidase.

(Method for Producing Food to which γ-Glutamyl Peptide is Added)

In another aspect, the present invention also provides a method of producing a food to which body taste is imparted, including adding a peptide having a γ-glutamyl bond number of 2 to 4 and a peptide chain length of γ-glutamyl bond number +1 to +2 (hereinafter referred to as γ-glutamyl peptide of this embodiment), or a salt thereof, to a food or a raw material of food.

In this embodiment, γ-glutamyl peptide or a salt thereof may be added to and contained in a food or a raw material of food, as the body taste-imparting agent described above. In addition, by applying the above-described method for producing γ-glutamyl peptide by enzymatic reaction, amino acid and enzyme or microorganism, which may be used for the production of γ-glutamyl peptide, may be added to a food or a raw material of food. That is, the γ-glutamyl peptide may be contained in the food or the raw material of the food by producing the γ-glutamyl peptide in the production stage of the food. In this case, the enzyme may be deactivated by means such as heating at an appropriate time in the production stage of the food. Alternatively, it may be a food in which the enzyme activity remains.

In this embodiment, an adding amount of γ-glutamyl peptide or a salt thereof is not particularly limited as long as a body taste-imparting effect is obtained, and may be adjusted as appropriate. For example, it may be added in an amount of 0.1 ppm to 5000 ppm (0.5%) as a conversion value to the amount of γ-glutamyl peptide to the food or raw material thereof. Examples of preferred adding amount include, for example, 0.5 to 5000 ppm, 1 to 5000 ppm, 10 to 5000 ppm, 100 to 5000 ppm, 250 to 5000 ppm, 1000 to 5000 ppm, 0.1 to 3000 ppm, 0.5 to 3000 ppm, 1 to 3000 ppm, 10 to 3000 ppm, 100 to 3000 ppm, 250 to 3000 ppm, 1000 to 3000 ppm, 0.1 to 1000 ppm, 0.5 to 1000 ppm, 1 to 1000 ppm, 10 to 1000 ppm, 100 to 1000 ppm, 250 to 1000 ppm, 0.1 to 500 ppm, 0.5 to 500 ppm, 1 to 500 ppm, 10 to 500 ppm and 100 to 500 ppm. In addition, when the component forms a salt, the adding amount of the γ-glutamyl peptide is calculated by converting the mass of the salt into the mass of an equimolar free form.

In this embodiment, the timing and the number of times of adding γ-glutamyl peptide or salt thereof are not particularly limited. And, it may be added in any step of the production or may be added to the final product. Further, in this embodiment, the method of adding γ-glutamyl peptide or a salt thereof is not particularly limited. For example, it may be mixed with other raw material, it may be added as an individual raw material, or it may be added by immersing a food into a liquid form of body taste-imparting agent. In this embodiment, the γ-glutamyl peptide or a salt thereof may be added once, or may be added in two or more portions. In this embodiment, one type, or two or more types, of γ-glutamyl peptide or a salt thereof may be added.

The description of the typical structure, the method of producing or obtaining, method of purification, free form and salt form of the γ-glutamyl peptide described in the aspect of the above-mentioned body taste-imparting agent is all applied in the γ-glutamyl peptide in this embodiment. In addition, in this embodiment, when γ-glutamyl peptide is added as the body taste-imparting agent, the description of the raw material, form, and addition amount of the body taste-imparting agent described in the above-mentioned aspect is applied to the body taste-imparting agent used in the production method of this aspect. Further, the description of the food to which the body taste-imparting agent described in the above-described aspect is added applies to the food to be subjected to the production method of this aspect.

(Method for Imparting Body Taste to Food)

In another aspect, the present invention also provides a method for imparting a body taste to a food, including adding a peptide having a γ-glutamyl bond number of 2 to 4 and a peptide chain length of γ-glutamyl bond number +1 to +2 (hereinafter also referred to as γ-glutamyl peptide of this embodiment), or a salt thereof, to a food or a raw material of the food.

In this embodiment, γ-glutamyl peptide or a salt thereof may be added to and contained in a food or a raw material of food, as the body taste-imparting agent described above. In addition, by applying the above-described method for producing γ-glutamyl peptide by enzymatic reaction, amino acid and enzyme or microorganism, which may be used for the production of γ-glutamyl peptide, may be added to a food or a raw material of food. That is, the γ-glutamyl peptide may be contained in the food or the raw material of the food by producing the γ-glutamyl peptide in the production stage of the food. In this case, the enzyme may be deactivated by means such as heating at an appropriate time in the production stage of the food. Alternatively, it may be a food in which the enzyme activity remains.

The description of the typical structure, the method of producing or obtaining, method of purification, free form and salt form of the γ-glutamyl peptide described in the aspect of the above-mentioned body taste-imparting agent is all applied in the γ-glutamyl peptide in this embodiment. In addition, in this embodiment, when γ-glutamyl peptide is added as the body taste-imparting agent, the description of the raw material, form, and addition amount of the body taste-imparting agent described in the above-mentioned aspect is applied to the body taste-imparting agent used in the method of this aspect. Further, the description of the food to which the body taste-imparting agent described in the above-described aspect is added applies to the food to be subjected to the method of this aspect. Moreover, the explanation of the adding amount, timing and number of times of adding γ-glutamyl peptide or a salt thereof described in the embodiment of the method for producing a food to which γ-glutamyl peptide is added is applied to the method of this embodiment.

EXAMPLES

Hereinafter, embodiments of the present invention will be described more specifically by way of examples.

Example 1: Preparation of γ-Glutamyl Peptide

As peptide samples, γ-Glu-Tyr (Bachem AG), γ-Glu-Val-Gly (Wako Pure Chemical Industries, Ltd.), γ-Glu-γ-Glu-Tyr (consignment synthetic product), γ-Glu-γ-Glu-Val (consignment synthetic product), γ-Glu-γ-Glu-Glu-Tyr (consignment synthetic product), γ-Glu-γ-Glu-γ-Glu-Tyr (consignment synthetic product), γ-Glu-γ-Glu-γ-Glu-γ-Glu-Tyr (consignment synthetic product), and γ-Glu-γ-Glu-γ-Glu-X (where X is Ala, Gly, Glu, Gln, Cys, Asp, Asn, Arg, His, Ile, Leu, Lys, Met, Phe, Pro, Trp, Ser, Thr or Val, consignment synthetic product) were used.

Example 2: Evaluation of Body Taste-Imparting Effect of γ-Glutamyl Peptide

Umami solution containing 0.7% MSG-0.4% NaCl and Sweet taste solution containing 6% sucrose were used as controls (3 points). And, sample solution was prepared by adding each γ-glutamyl peptide to the control. As comparative controls, γ-Glu-Val-Gly disclosed in Patent Document 1 and Patent Document 6 were used. The panelists were 7 trained panelists at Fuji Oil Holdings Inc. And, the panelist evaluated a body taste of from initial taste to middle taste, a thickness of from middle taste to aftertaste, and persistence with the following five levels. The results of average score calculated from the evaluations are shown in Table 1.
5 points: feels much stronger than the control
4 points: feels stronger than the control
3 points: feels the same as the control
2 points: feels a little weaker than the control
1 point: feels much weaker than the control

TABLE 1

Comparison of taste-improving effect of each γ-glutamyl peptides

| Components | Umami solution | | Sweet taste solution | |
|---|---|---|---|---|
| | Initial-middle taste | Middle-after taste | Initial-middle taste | Middle-after taste |
| Control | 3.0 | 3.0 | 3.0 | 3.0 |
| γ-Glu-Tyr | 3.5 | 3.9* | 3.5 | 3.9* |
| γ-Glu-γ-Glu-Tyr | 4.0* | 3.9* | 4.0* | 3.7* |
| γ-Glu-γ-Glu-γ-Glu-Tyr | 4.1* | 4.0* | 4.3* | 4.3* |
| γ-Glu-γ-Glu-γ-Glu-γ-Glu-Tyr | 3.9* | 3.7 | 3.9* | 3.6 |
| γ-Glu-Val-Gly | 3.6 | 4.8* | 3.6 | 4.3* |

*Significant difference with control at 5% risk rate.

As shown in Table 1, γ-Glu-Tyr and γ-Glu-Val-Gly imparted little body taste of from the initial taste to middle taste. And, the taste from the middle taste to aftertaste was strong, resulting in persistent of the strong aftertaste. In addition, γ-Glu-γ-Glu-γ-Glu-γ-Glu-Tyr having four γ-glutamyl bonds gave a good result that sufficiently imparted a body taste of from the initial taste to the middle taste. Further, γ-Glu-γ-Glu-Tyr having two γ-glutamyl bonds and γ-Glu-γ-Glu-γ-Glu-Tyr having three γ-glutamyl bonds, gave an excellent result that emphasizes the taste both of from the initial taste to the middle taste and the middle taste to the aftertaste, and imparted the body taste overall, but the persistence of the aftertaste was suppressed. In particular, peptide having three γ-glutamyl bonds gave very good results for both umami and sweet taste solutions.

Figures 3, 4:
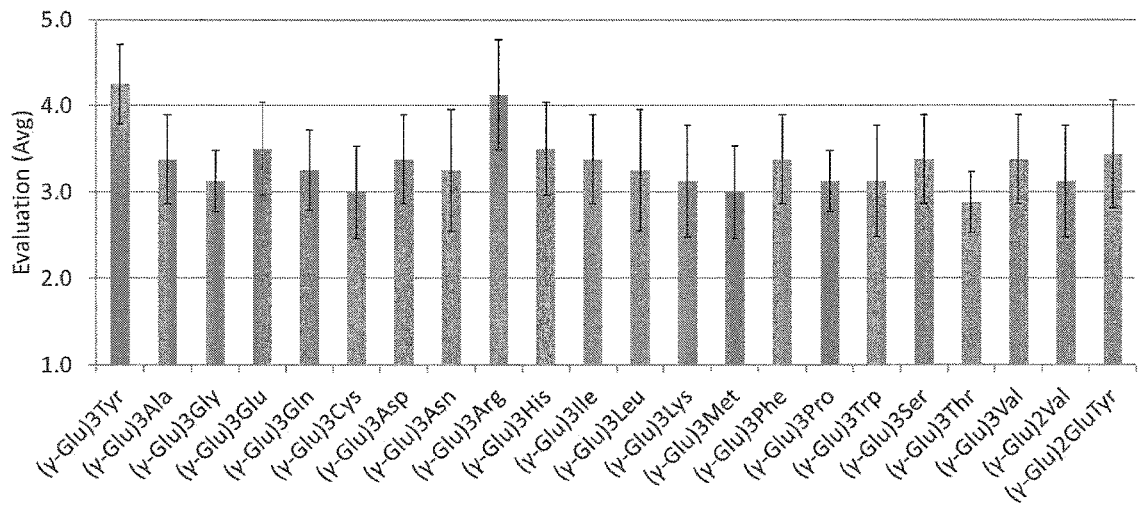
FIG. 3 It is a graph showing the result of sensory evaluation of Example 3.
FIG. 4 It is a figure showing detailed data of the sensory evaluation of Example 3.

Example 3: Evaluation of Body Taste-Imparting Effect of γ-Glutamyl Tripeptide on Sweet Taste Sweet taste solution containing 6% sucrose was used as a control (3 points). And, sample solution was prepared by adding 100 ppm of each γ-glutamyl tripeptide to the control. As comparative controls, γ-Glu-γ-Glu-Val and γ-Glu-γ-Glu-α-Glu-Tyr were used. The panelists were eight trained panelists at Fuji Oil Holdings Inc. And, the panelist evaluated a body taste of from initial taste to middle taste with the following five levels. The results of average score calculated from the evaluations are shown in FIG. 3 and Table 1.
5 points: feels much stronger than the control
4 points: feels stronger than the control
3 points: feels the same as the control
2 points: feels a little weaker than the control
1 point: feels much weaker than the control

TABLE 2

Comparison of taste-improving effect of each γ-glutamyl peptides

| Components | Sweet taste solution Initial-middle taste |
|---|---|
| Control | 3.0 |
| γ-Glu-γ-Glu-γ-Glu-Tyr | 4.3** |
| γ-Glu-γ-Glu-γ-Glu-Ala | 3.4 |
| γ-Glu-γ-Glu-γ-Glu-Gly | 3.1 |
| γ-Glu-γ-Glu-γ-Glu-Glu | 3.5* |
| γ-Glu-γ-Glu-γ-Glu-Gln | 3.3 |
| γ-Glu-γ-Glu-γ-Glu-Cys | 3.0 |
| γ-Glu-γ-Glu-γ-Glu-Asp | 3.4 |
| γ-Glu-γ-Glu-γ-Glu-Asn | 3.3 |
| γ-Glu-γ-Glu-γ-Glu-Arg | 4.1** |
| γ-Glu-γ-Glu-γ-Glu-His | 3.5* |
| γ-Glu-γ-Glu-γ-Glu-Ile | 3.4 |
| γ-Glu-γ-Glu-γ-Glu-Leu | 3.3 |
| γ-Glu-γ-Glu-γ-Glu-Lys | 3.1 |
| γ-Glu-γ-Glu-γ-Glu-Met | 3.0 |
| γ-Glu-γ-Glu-γ-Glu-Phe | 3.4 |
| γ-Glu-γ-Glu-γ-Glu-Pro | 3.1 |
| γ-Glu-γ-Glu-γ-Glu-Trp | 3.1 |
| γ-Glu-γ-Glu-γ-Glu-Ser | 3.4 |
| γ-Glu-γ-Glu-γ-Glu-Thr | 2.9 |
| γ-Glu-γ-Glu-γ-Glu-Val | 3.4 |
| γ-Glu-γ-Glu-Val | 3.1 |
| γ-Glu-γ-Glu-Glu-Tyr | 3.4 |

*Significant difference with control at 5% risk rate.
**Significant difference with control at 1% risk rate.

As shown in FIG. 3 and Table 2, it was found that peptides having three γ-glutamyl bonds have high and low body taste-imparting effects due to the difference in terminal amino acid. Peptides having three γ-glutamyl bonds that were particularly effective include γ-Glu-γ-Glu-γ-Glu-Tyr and γ-Glu-γ-Glu-γ-Glu-Arg, then γ-Glu-γ-Glu-γ-Glu-Ala, γ-Glu-γ-Glu-γ-Glu-Glu, γ-Glu-γ-Glu-γ-Glu-Asp, γ-Glu-γ-Glu-γ-Glu-His, γ-Glu-γ-Glu-γ-Glu-Ile, γ-Glu-γ-Glu-γ-Glu-Leu, γ-Glu-γ-Glu-γ-Glu-Phe, γ-Glu-γ-Glu-γ-Glu-Ser and γ-Glu-γ-Glu-γ-Glu-Val. In addition, as with Tyr, γ-Glu-γ-Glu-γ-Glu-Val is superior to γ-Glu-γ-Glu-Val in the effect of imparting a body taste of from the initial taste to the middle taste. Furthermore, an effect was also observed with a γ-glutamyl peptide having two γ bonds and one α bond, such as γ-Glu-γ-Glu-α-Glu-Tyr.

Example 4: Effect of Adding Body Taste-Imparting Agent to Various Foods (Preparation of Body Taste-Imparting Agent)
As a body taste-imparting agent, a mixture of 33% (w/w) γ-Glu-Tyr (product of Bachem AG); 43% (w/w) γ-Glu-γ-Glu-Tyr (consignment synthetic product); 17% (w/w) γ-Glu-γ-Glu-γ-Glu-Tyr (consignment synthetic product); and 7% (w/w) γ-Glu-γ-Glu-γ-Glu-γ-Glu-Tyr (consignment synthetic product) was prepared. The body taste-imparting agent was added to various foods shown in the table below at a content of 250 ppm. The panelists were six trained panelists at Fuji Oil Holdings Inc. And, the panelist evaluated a body taste compared to the additive-free product with the four levels (0-3 points, 3 points: feels much stronger than additive-free product, 2 Points: feels stronger than additive-free product, 1 point: comparable to additive-free product, 0 point: feels weaker than additive-free product). The average score was calculated, with the average score being 2 or more and 3 or less as "○", 1 or more and less than 2 as "Δ", and 0 or more and less than 1 as "x". The results are shown in the table below.

TABLE 3

| Food | Product name | Manufacturer | Evaluation |
|---|---|---|---|
| Japanese-style food | | | |
| Low-sodium miso | Taste of Ryotei, additive-free, low-sodium | Marukome Co., Ltd. | ○ |
| Low-sodium soy sauce | Low-sodium soy sauce | Kikkoman Corporation | Δ |
| Noodle soup | Noodle soup of Somi | Somi Shokuhin Co., Ltd. | Δ |
| Western-style food | | | |
| Western-style soup | Tomato potage soup | Ajinomoto Co., Inc. | ○ |
| Western-style soup | Corn cream soup | Ajinomoto Co., Inc. | ○ |
| Western-style soup | Clam chowder | Ajinomoto Co., Inc. | ○ |
| Western-style sauce | Demi-glace sauce | Kewpie Corporation | ○ |
| Western-style sauce | White sauce | Heinz Japan Ltd. | ○ |
| Western-style sauce | Carbonara, rich cheese | Kewpie Corporation | ○ |
| Western-style sauce | Meat sauce | Kewpie Corporation | ○ |
| Mayonnaise | Kewpie calorie half | Kewpie Corporation | ○ |
| Chinese-style food | | | |
| Ramen soup | Hokkaido ramen soup, soy sauce taste | Kikusui Co., Ltd. | Δ |
| Chinese-style dressing | Gold sesame sauce, calorie half | Mizkan Co., Ltd. | ○ |
| Chinese-style sauce | Mapo-tofu mix | Marumiya Corporation | Δ |
| Chinese-style sauce | Oyster sauce | Youki Food Co., Ltd. | Δ |
| Chinese-style soup | Chicken broth mix | Ajinomoto Co., Inc. | Δ |
| Asian-style food | | | |
| Asian-style soup | Tom yam kung | Pokka Sapporo Food & Beverage Ltd. | Δ |
| Asian-style curry | Green curry soup | Pokka Sapporo Food & Beverage Ltd. | Δ |
| Dairy product, fermented dairy product | | | |
| Milk | Tasty skimmed milk | Meiji Co., Ltd. | ○ |
| Yogurt | RI yogurt, low fat | Meiji Co., Ltd. | ○ |
| Yogurt | Bifix yogurt, non-fat | Ezaki Glico Co., Ltd. | ○ |
| Yogurt beverage | RI drink, low sugar, low calorie | Meiji Co., Ltd. | ○ |
| Lactic beverage | Yakult calorie half | Yakult Honsha Co., Ltd. | ○ |
| Lactic beverage | Calpis calorie half | Asahi Soft Drinks Co., Ltd. | ○ |
| Coffee beverage | | | |
| Coffee beverage | Georgia Emerald Mountain blend | Coca-Cola (Japan) company, Limited | ○ |
| Coffee beverage | Wonda Morning Shot | Asahi Soft Drinks Co., Ltd. | ○ |
| Coffee beverage | Fire, Freshly Ground from Workshop | Kirin Beverage Company, Limited | ○ |
| Coffee beverage | DyDo Blend | DyDo Drinco. | ○ |
| Coffee beverage | Boss Luxury Low Sugar | Suntory Beverage & Food Limited | ○ |
| Coffee beverage | Milk Coffee | UCC Ueshima Coffee Co., Ltd. | ○ |
| Confectionery, cream | | | |
| Chocolate | Ice Coating 175 | Fuji Oil Co., Ltd. | ○ |
| Chocolate | Chocolate Sauce | Fuji Oil Co., Ltd. | Δ |
| Cream | Topping VND | Fuji Oil Co., Ltd. | ○ |
| Cream | Legere 20 | Fuji Oil Co., Ltd. | Δ |
| Cream | Clear Whip 15ND | Fuji Oil Co., Ltd. | Δ |
| Soybean product | | | |
| Soybean food | Mame-Dore (soy cream dressing) | Fuji Oil Co., Ltd. | Δ |
| Soybean food | Cheese-like material | Fuji Oil Co., Ltd. | ○ |

TABLE 3-continued

| Food | Product name | Manufacturer | Evaluation |
|---|---|---|---|
| Soybean food | Mame-Mage, (cream cheese-like soy cheese) | Fuji Oil Co., Ltd. | Δ |
| Soymilk | Kibun Plain soymilk | Kikkoman Corporation | ○ |
| Soymilk | Bimi-Tonyu, (low fat soymilk) | Fuji Oil Co., Ltd. | ○ |
| Soymilk | Kokuream (soy cream) | Fuji Oil Co., Ltd. | ○ |
| Soy protein material | Soyafit 2000 (defatted soymilk powder) | Fuji Oil Co., Ltd. | ○ |

For Japanese-style foods, favorable effect was obtained in miso, and an effect was also obtained in soy sauce. For Western-style foods, it was very compatible with all flavors, such as various soups and sauces, and a strong body taste and kokumi were added. For Chinese-style foods, most favorable effect was obtained in sesame dressing, and the effects were obtained in other flavors. For Asian-style food, spicy taste tends to mask the effect of imparting body taste, but certain effect was obtained.

In addition, it was very compatible with dairy products and fermented dairy products, and a strong body taste and kokumi were added. For coffee beverages, a strong body taste and kokumi were added. For chocolate, a high effect was obtained particularly when the lipid content was high. For creams, it was particularly effective for pure plant products. For soybean foods, basically favorable results were obtained. In particular, the effects on soy milk, defatted soymilk powder, and low fat soy milk were very high.

INDUSTRIAL APPLICABILITY

According to the present invention, a body taste-imparting agent for a food may be obtained. The body taste-imparting agent of the present invention may be used in the fields such as food, seasoning, functional food and food service industry.

The invention claimed is:

1. A method for imparting a body taste to a food, comprising adding a peptide consisting of γ-Glu-γ-Glu-X, or a peptide consisting of γ-Glu-γ-Glu-γ-Glu-X, or a peptide consisting of γ-Glu-γ-Glu-γ-Glu-γ-Glu-X, or a salt thereof to a food or a raw material of the food,
wherein X is an amino acid selected from the group consisting of Tyr, Ala, Asp, Asn, Arg, His, Ile, Leu, Phe and Ser.

2. The method according to claim 1, wherein X is Tyr or Arg.

3. The method according to claim 1, wherein X is an amino acid selected from the group consisting of Tyr, Ala, Asp, Asn, Arg, His, Leu, Phe and Ser.

4. The method according to claim 1, wherein X is Tyr.

5. The method according to claim 1, wherein the peptide consists of γ-Glu-γ-Glu-X, and wherein X is an amino acid selected from the group consisting of Tyr, Ala, Asp, Arg, His, Phe and Ser.

6. A method for imparting a body taste to a food, comprising adding a peptide consisting of γ-Glu-γ-Glu-γ-Glu-X, or a peptide consisting of γ-Glu-γ-Glu-γ-Glu-γ-Glu-X, or a salt thereof to a food or a raw material of the food,
wherein X is an amino acid selected from the group consisting of Tyr, Ala, Glu, Gln, Asp, Asn, Arg, His, Ile, Leu, Phe, Ser and Val.

7. The method according to claim 6, wherein X is Tyr or Arg.

8. The method according to claim 6, wherein X is an amino acid selected from the group consisting of Tyr, Ala, Asp, Asn, Arg, His, Leu, Phe and Ser.

9. The method according to claim 6, wherein X is Tyr.

10. The method according to claim 6, wherein the peptide consists of γ-Glu-γ-Glu-γ-Glu-X, and wherein X is an amino acid selected from the group consisting of Tyr, Ala, Glu, Gln, Asp, Asn, Arg, His, Ile, Leu, Phe and Ser.

11. The method according to claim 9, wherein the peptide consists of γ-Glu-γ-Glu-γ-Glu-X, and wherein X is an amino acid selected from the group consisting of Tyr, Ala, Glu, Gln, Asp, Asn, Arg, His, Leu, Phe and Ser.

12. The method according to claim 6, wherein the peptide consists of γ-Glu-γ-Glu-γ-Glu-γ-Glu-X, and wherein X is an amino acid selected from the group consisting of Tyr, Glu, Arg and His.

* * * * *